United States Patent [19]

Kataoka et al.

[11] 4,406,470
[45] Sep. 27, 1983

[54] CHUCK DEVICE FOR DENTAL HANDPIECE

[75] Inventors: Kenzo Kataoka, Ugi; Hiroo Watanabe; Haruo Ogawa, both of Kyoto, all of Japan

[73] Assignee: Kabushiki Kaisha Morita Seisakusho, Kyoto, Japan

[21] Appl. No.: 319,722

[22] Filed: Nov. 9, 1981

Related U.S. Application Data

[63] Continuation of Ser. No. 89,563, Oct. 29, 1979, abandoned.

[30] Foreign Application Priority Data

Oct. 27, 1978 [JP]  Japan ............................ 53-148419

[51] Int. Cl.³ .......................................... B23B 31/08
[52] U.S. Cl. ................................. 279/1 SG; 279/1 Q; 433/127
[58] Field of Search .......... 409/233, 234; 279/1 SG, 279/1 SJ, 1 Q; 433/127, 129

[56] References Cited

U.S. PATENT DOCUMENTS 2,426,200  8/1947  Green .............................. 279/1 Q
4,189,836  2/1980  Sugai et al. ...................... 433/127

Primary Examiner—William R. Briggs
Attorney, Agent, or Firm—Koda and Androlia

[57] ABSTRACT

A chuck device for a dental handpiece comprising fixedly mounting a front collar inside a rotor at the end thereof for the dental handpiece and threadedly and detachably fixing a cartridge chuck behind said front collar inside of said rotor, said cartridge chuck comprising a substantially cylindrical chuck case provided at the rear end with an engagement portion for detachably connecting a cutting tool thereto, a synthetic rubber chuck body press inserted into the end side of said case, and a rear collar fixedly mounted behind said chuck body inside said case.

6 Claims, 4 Drawing Figures

CHUCK DEVICE FOR DENTAL HANDPIECE

This is a continuation of application Ser. No. 89,563 filed Oct. 29, 1979 abandoned.

BACKGROUND OF THE INVENTION

1. Field of the Invention

This invention relates to a chuck device for a dental handpiece.

2. Prior Art

Conventionally, there have been various types of chuck devices of this kind available commercially, but because they are either large in deflection of axis of a cutting tool shaft or high insertion pressure when the cutting tool is inserted, they present a number of problems such as the bent shaft of a cutting tool, a broken cutting edge, lack of durability, short service life, etc. In the case of such chuck devices it is usually necessary to send the handpiece back to a factory specializing in the production of such chuck devices, either to repair or replace the chuck in question each time replacement of the chuck is needed. The inconvenience involved is very great. In view of such circumstances, a so-called cartridge type collect chuck which premits replacement of chucks by users themselves and which is relatively high in durability is used by some users, but even this collect type chuck still has the fatal disadvantage that the chuck needs the trouble of tightening and loosening the screw everytime the cutting tool is attached and detached and that it has a possibility of the cutting tool being flung out to cause accidents when tooth cutting is carried out without sufficiently tightening the screw.

SUMMARY OF THE INVENTION

In view of the Prior Art described above, this invention has for its object the provision of a very useful check device which is readily replaceable by the user, is easily attached and detached, the cutting tool is small in the axial deflection of the cutting tool shaft attached and has excellent durability. A preferred embodiment of the invention will now be described in detail, by way of example only, in conjunction with the accompanying drawings.

DETAILED DESCRIPTION OF THE INVENTION

Figure 1:
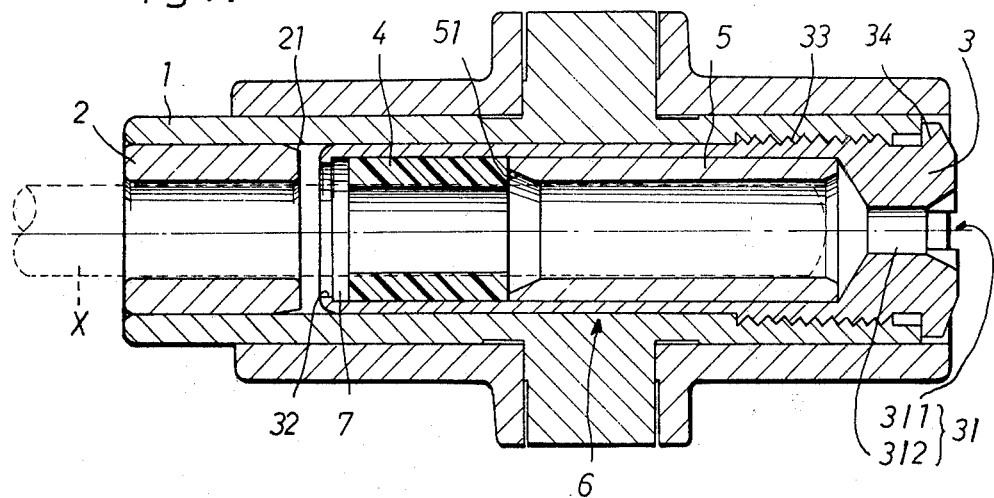
FIG. 1 is a cross-sectional elevational view of a preferred embodiment of the chuck device of the present invention.
Figure 2:
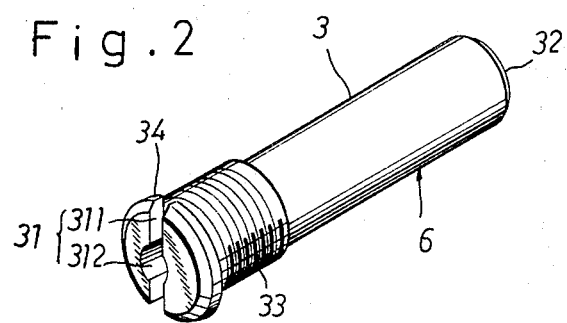
FIG. 2 is a perspective view of a cartridge chuck alone detached from the chuck device.

As shown in FIGS. 1 and 2, the chuck device of the present invention basically comprises fixedly mounting a front collar 2 inside of a rotor 1 at the end thereof for a dental handpiece and threadedly and detachably fixing a cartridge chuck 6 behind the front collar 2 inside of the rotor 1. The chuck 6 including a substantially cylindrical chuck case 3 provided at the rear end with an engagement portion 31 for detachably connecting a cutting tool thereto, a synthetic rubber chuck body 4 press inserted into the end side of the case 3, and a rear collar 5 fixedly mounted behind the chuck body 4 inside the case 3.

Figure 3:
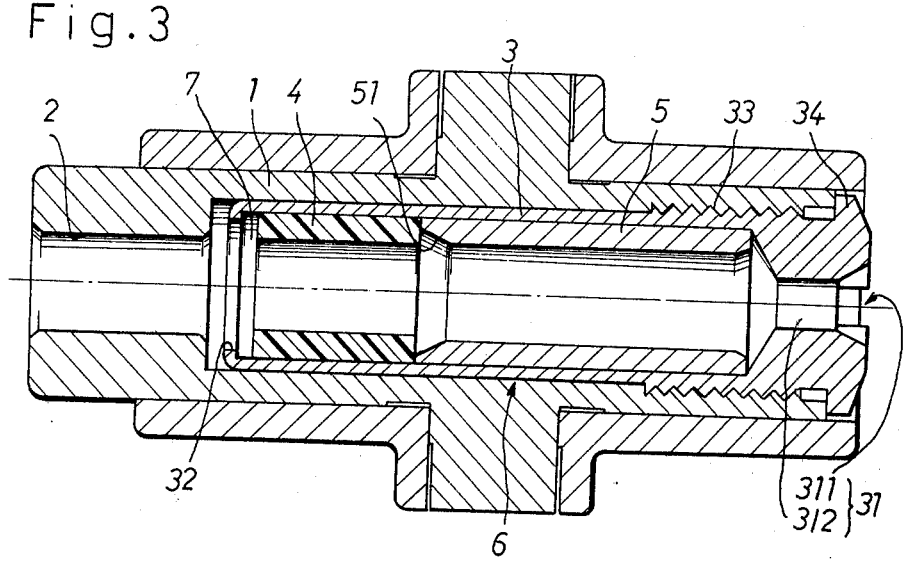
FIG. 3 is a cross-sectional elevational view of another preferred embodiment of the chuck device according to the present invention.

The above front collar 2 is intended to minimize the deflection of axis of the cutting tool shaft X in time of rotation, and is preferably made of wear resisting cemented carbide alloy. In the embodiment shown in FIG. 1, the front collar 2 is cylindrical in shape such that it has an outer diameter equal to the inner diameter of the rotor 1 and the inner diameter is slightly larger than the shaft diameter of the cutter tool shaft and is press inserted and fixed to the end portion of the inside of the rotor 1. In this manner, when the collar 2 is press inserted and secured to the end portion, it is desirable to form a tapered surface on the outer perhphery of the inserted end edge of the front collar 2 so as to facilitate press insertion. The front collar 2 of the type described above needs no replacement, and accordingly as shown in the embodiment in FIG. 3, the collar 2 may be formed integrally with the rotor 1. The front collars in FIGS. 1 and 3, as described above, function to prevent deflection of the cutting tool shaft X in time of rotation, and at the same time, for example, when the cutting tool shaft X is bent, or when the tool shaft is increased in diameter because of its corrosion, insertion of the tool becomes impossible, and accordingly, if there is produced this kind of deflection which has an adverse effect especially on the bearing element of the handpiece, such deflection can readily be detected, which fact is also an advantage of the present invention.

On the other hand, the cartridge chuck 6 is made-up of a synthetic rubber chuck body 4 and a rear collar 5 contained in a substantially cylindrical chuck case 3. The chuck case 3 is provided at the rear end with an engagement portion 31 for detachably fixing the tool. The portion 31 comprises a groove 311 and an opening 312 formed in the center of the groove such as those shown in FIG. 2, and is formed at its thick-walled outer periphery with a threaded connection surface 33 and is threadedly fixed behind the front collar 2 in the rotor 1. The cartridge chuck 6 is adapted to be readily attached and detached for replacement by bringing a suitable tool for use in connection and disconnection, such as a screwdriver, into engagement with the engagement portion 31 of the chuck case 3 by tightening and loosening the screw. In the cartridge chuck 6 of the kind described it is desirable to contemplate for the prevention of the chuck body 4 in the chuck case 3 against slipping out from the case 3 by either caulking the end edge 32 of the case 3 inwardly as shown or cutting threads or grooves on the inside surface of the chuck case 3 (particularly on the surface to be pressed into contact with the chuck body 4), or press inserting a concentric ring (not shown) for prevention of slipping out of the chuck body 4 in front of the chuck body 4 inside the chuck case 2 and is also desirable to contemplate to prevent overtightening the screw in time of threadedly fixing the cartridge chuck 6 by forming a flange 34 at the rear end of the chuck case 3 in various ways, it is desirable to make the chuck case 3 of a material relatively superior in workability such as high tension brass.

The synthetic rubber chuck body 4 of the cartridge chuck 6 is intended to grip the cutting tool shaft X so as to prevent the tool from slipping out of position and is made in a cylindrical form preferably of nitrile rubber, urethane rubber, silicone rubber, fluorine rubber, etc.

which are excellent in wear resistance and least subject to change due to aging. The body 4 is adjusted in such a manner that the inner diameter of the body 4 is slightly smaller than the diameter of the cutting tool shaft X so that the tool will not fall out of the chuck body 4 when the body 4 is press inserted into the chuck case 3 at the end side thereof. Accordingly, the force necessary for detachably fixing the tool is far smaller than that needed by the conventional friction type chucks. It is desirable to prevent the increase and decrease of the cutting tool in attaching and detaching force so as to permit the insertion and withdrawal of the cutting tool shaft X by constant force and to prevent the chuck body 4 against axial sliding by cutting threads or grooves on the inner surface of the chuck case 3 (particularly on the surface to be pressed into contact with the body 4), as earlier described, so as to prolong the service life of the chuck body 4. Therefore, the chuck body 4 of this type is pressed to be enlarged and rolled when the cutting tool shaft X is inserted, and in order to give relief to such enlargement and rolling, it is desirable to form a space 7 in front of the chuck body 4 inside the chuck case 3 and to form a chamfer or relief 51 as shown at the end edge at which a rear collar 5 is in contact with the chuck body 4.

Figure 4:
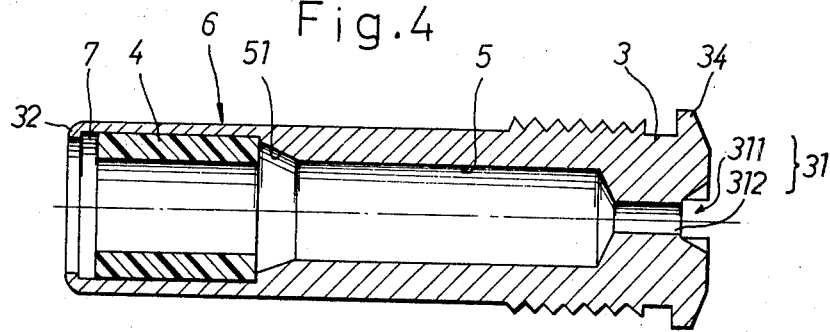
FIG. 4 is a cross-sectional elevational view of a cartridge chuck alone detached from the chuck device shown in FIG. 3.

The rear collar 5 of the cartridge chuck 6, in cooperation with a front collar 2, functions as a guide for bringing the inserted cutting tool shaft X into parallelism with the rotor 1. The collar 5 is preferably made as of austenite stainless steel in such a cylindrical shape in which the collar 5 has an outer diameter equal to the inner diameter of the chuck case 3 and an inner diameter very slightly larger than the diameter of the cutting tool shaft X. The collar 5 is press inserted into the chuck case 3 and secured behind the chuck body 4 in the chuck case 3, and the chamfer or relief 51 earlier described is formed at the end edge at which the collar 5 is in contact with the chuck body 4. The collar of the type described may be formed integrally with the chuck case 3 as shown in FIG. 4. Forming of the collar 5 integrally with the case 3 reduces the complexity of dimensional agreement involved in the separate or independent making of the rear rollar 5 in a substantial degree and can also dispose with a step of press inserting the collar 5 into the chuck case 3 and fixing the same to the chuck case 3. That is an advantage.

According to the chuck device of the invention constructed as above, it is only necessary to insert the cutting tool shaft X through the opening at the end of the front collar 2 to mount the cutting tool. Conversely, all that is necessary to detach the cutting tool is to withdraw the tool from the case 3 as by pliers or to insert a pin or the like into the hole 312 of the case 3 to push the tool out of the case 3. Thus, the chuck device is very easy of attachment and detachment of the cutting tool, and relieves the user of the trouble to tighten and loosen the screw every time the toll is detached and attached unlike the case of the conventional collet type chucks wherein the tightening and loosening of the screw are necessary. At the same time, the device can prevent any possibility of the tool being flung out during rotation because tightening of the screw was inadvertently forgotten or the screw got loosened.

In addition thereto, since parallelism of the cutting tool shaft X with the rotor 1 is provided by the front collar 2 and rear collar 5 in the device of the invention, the chuck device of the invention is far higher in accuracy than the conventional type chuck wherein parallelism is maintained by the chuck body alone. The accuracy is such that for example, when the chuck with a cutting tool 20 $\mu$mm long and 1.595 mm$\phi$ in shaft diameter is turned 200,000 to 500,000 rpm, there is produced a deflection of axis of the order of 15 to 20 in the conventional type chucks, but the deflection in the invention is so very small as up to 12$\mu$. Furthermore, the cylindrical synthetic rubber chuck body 4 used in the invention is smaller than the conventional friction type chucks in the force required for attaching and detaching the cutting tool, and is superior also in durability. Particularly, provision of threads and groove on the inner surface of the chuck case 3 to prevent the chuck body 4 against axial sliding, or provision of the space 7 for relief in front of the chuck body 4 inside the chuck case and formation of the chamfer or relief 51 for the likewise intended relief at the end edge of the rear collar 5 at which the collar is in contact with the chuck body 4 make it possible to attach and detach the cutting tool by constant force and prolong the service life of the chuck body 4 in such a substantial degree that, even when the tool is subjected to rough use by its very frequent attachment, detachment or replacement, the chuck body 4 can stand use as long as at least more than half a year. When the chuck body 4 is reduced in function by the effect of long use and has to be replaced, the user himself can easily replace the whole of the cartridge chuck 6 by application of a tool adapted for attachment and detachment to the engagement portion 31 of the chuck case 3, and is completely relieved from the inconvenience with which the user had the trouble to send the chuck device to the factory concerned for replacement as was the practice with the conventional type chuck device. In addition thereto, provision of the front collar 2 independent of the cartridge chuck 6, as in the invention, makes it unnecessary to replace the front collar, thus bringing about an economical advantage by reducing the cost of the cartridge chuck to that amount. Also, provision of the front collar 2 inside the rotor 1 at the end thereof brings about an additional benefit in that the user can readily locate any defect of the cutting tool because insertion of the tool becomes impossible when something is wrong with the cutting tool such as bending of the cutting tool shaft or an increase in diameter by corrosion of the shaft. Furthermore, inward bending of the end edge 32 of the chuck case 3, press insertion of the concentric ring in front of the chuck body 4 inside the chuck case 3, and formation of threads and grooves on the inner surface preclude any possibility of the chuck body 4 slipping out of position when the cutting tool shaft X is withdrawn. Also, formation of the flange 34 at the rear end of the chuck case 3 has the additional advantage of preventing the cartridge chuck 6 against overscrewing when the screw of the chuck 6 is tightened.

As particularly described above, the chuck device of this invention has numerous marked effects and greatly contributes to dental practice.

It should be apparent to one skilled in the art that the above described embodiments are merely illustrative of but a few of the many possible specific embodiments which represent the application of the principles of the present invention. Numerous and varied other arrangements can be readily devised by those skilled in the art without departing from the spirit and scope of the invention.

We claim:

1. A detachable cartridge chuck for a dental handpiece of the type including an air rotor having a cylindrical opening provided axially thereof and a front cutting tool collar of wear resisting material or wear resisting cemented carbide alloy housed in one end of said cylindrical opening, said cartridge chuck comprising:
- a cylindrical chuck case for insertion into said cylindrical opening in said rotor and which is threadably coupled to said air rotor by threadably engaging with a threaded portion of such cylindrical opening;
- a rear cutting tool collar provided in said case adjacent said end of said case which is threadably coupled to said air rotor;
- a resilient chuck body provided in said case adjacent said rear cutting tool collar and between said front and rear collars when said case is threadably coupled to said air rotor;
- a chamfer formed in an end of said rear collar which is in contact with said chuck body;
- a means for retaining said chuck body in said case provided at an end of said case which is adjacent an end of said chuck body; and
- a tool engagement means provided in said end of said case which is threadably coupled to said air rotor whereby said chuck cartridge may be easily removed and replaced utilizing a tool to engage and disengage said threadably coupling.

2. A device according to claim 1 wherein said front collar is formed integrally with said rotor.

3. A device according to claim 1 or 2 wherein said cartridge chuck comprises said rear collar and said chuck case formed into one body.

4. A device according to claim 2 or 1 wherein said means for retaining said chuck body comprises said cartridge chuck caulked inwardly at an edge of the chuck case thereof.

5. A device according to claim 1 or 2, wherein said cartridge chuck has a space formed in front of the chuck body inside the chuck case thereof.

6. A device according to claim 2 or 1 wherein said tool engagement means further comprises an engagement portion adapted to detachably connect a cutting tool thereto at the rear end edge of the chuck case thereof, said engagement portion comprising a groove or square hole formed in the center of said groove.

* * * * *